(12) United States Patent
Glombik et al.

(10) Patent No.: US 7,179,792 B2
(45) Date of Patent: Feb. 20, 2007

(54) COMBINATION PRODUCT OF A 1,4-BENZOTHIEPINE 1,1-DIOXIDE COMPOUND WITH AT LEAST ONE OTHER ACTIVE INGREDIENT AND THE USE OF THE PRODUCT

(75) Inventors: Heiner Glombik, Hofheim (DE); Wendelin Frick, Huenstetten-Beuerbach (DE); Hans-Ludwig Schaefer, Hochheim (DE); Werner Kramer, Mainz-Laubenheim (DE)

(73) Assignee: Sanofi-Aventis Deulschland GmbH, Frankfurt am Main (DE)

( * ) Notice: Subject to any disclaimer, the term of this patent is extended or adjusted under 35 U.S.C. 154(b) by 0 days.

(21) Appl. No.: 10/699,967

(22) Filed: Nov. 3, 2003

(65) Prior Publication Data

US 2004/0097424 A1 May 20, 2004

Related U.S. Application Data

(63) Continuation of application No. 10/225,841, filed on Aug. 22, 2002, now abandoned.

(30) Foreign Application Priority Data

Aug. 22, 2001 (DE) ................. 101 40 169
Aug. 31, 2001 (DE) ................. 101 42 456

(51) Int. Cl.
A61K 38/06 (2006.01)
A61K 38/05 (2006.01)
A61K 38/04 (2006.01)
C07K 5/06 (2006.01)
C07K 5/04 (2006.01)

(52) U.S. Cl. ............... 514/18; 514/19; 514/23; 530/330; 530/331; 536/17.2

(58) Field of Classification Search ............ 514/18, 514/19, 23; 530/330, 331; 536/17.2
See application file for complete search history.

(56) References Cited

U.S. PATENT DOCUMENTS

| | | | |
|---|---|---|---|
| 5,190,923 | A | 3/1993 | Vincent et al. |
| 6,221,633 | B1 | 4/2001 | Ertl et al. |
| 6,221,897 | B1 * | 4/2001 | Frick et al. ........ 514/431 |
| 6,245,744 | B1 | 6/2001 | Frick et al. |
| 6,342,512 | B1 | 1/2002 | Kirsch |
| 6,380,230 | B1 | 4/2002 | Brodin et al. |
| 6,387,944 | B1 * | 5/2002 | Frick et al. ........ 514/431 |
| 6,441,022 | B1 * | 8/2002 | Frick et al. ........ 514/431 |
| 6,498,156 | B2 | 12/2002 | Glombik |
| 2003/0191174 | A1 | 10/2003 | Ikuta et al. |

FOREIGN PATENT DOCUMENTS

| | | |
|---|---|---|
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 00/40569 | 7/2000 |
| WO | WO 00/63208 | 10/2000 |
| WO | WO 00/66585 | 11/2000 |
| WO | WO 00/71549 | 11/2000 |
| WO | WO 00/78312 | 12/2000 |
| WO | WO 01/09111 | 2/2001 |
| WO | WO 01/85695 | 11/2001 |
| WO | WO 01/91752 | 12/2001 |

OTHER PUBLICATIONS

AHFS Drug Information, 1994, pp. 1096-1103.*
Castaner, R.M. et al Drugs of the Future, 2000, 25(7), 679-685.*
Castaner, R. M. et al, Drugs of the Future, 2000, 25(7), 679-685.*
Asakawa, A., et al., Cocaine-Amphetamine-Regulated Transcript Influences Energy Metabolism, Anxiety and Gastric Emptying in Mice, Hormone and Metabolic Research, 2001, vol. 33(9), pp. 554-558.
Lee Daniel W., et al., Leptin Agonists As A Potential Approach To The Treatment Of Obesity, Drugs Of The Future, (2001), vol. 26, No. 9, pp. 873-881.
Salvador Javier, et al., Perspectives in the Therapeutic Use of Leptin, Expert Opin. Pharmacother. (2001), vol. 2(10), pp. 1615-1622.
Zunft, H. et al., Carob Pulp Preparation for Treatment of Hypercholesterolemia, Advances in Therapy, 2001, vol. 18(5), pp. 230-236.

* cited by examiner

Primary Examiner—Shaojia Anna Jiang
Assistant Examiner—Ganapathy Krishnan
(74) Attorney, Agent, or Firm—James W. Bolcsak

(57) ABSTRACT

The present invention is directed to a 1,4-benzothiepine 1,1-dioxide compound of formula I

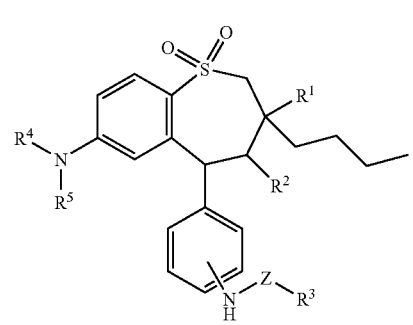

in which the radicals have the meanings defined herein, or a pharmaceutically acceptable salt or physiologically functional derivative thereof, with at least one other active ingredient, or a pharmaceutically acceptable salt or physiologically functional derivative thereof. The invention is also directed to the use of the combination product, pharmaceutical composition comprising the combination product and method for preparing the pharmaceutical composition.

7 Claims, No Drawings

COMBINATION PRODUCT OF A 1,4-BENZOTHIEPINE 1,1-DIOXIDE COMPOUND WITH AT LEAST ONE OTHER ACTIVE INGREDIENT AND THE USE OF THE PRODUCT

FIELD OF THE INVENTION

The present invention relates to a combination product of a 1,4-benzothiepine 1,1-dioxide compound of formula I, with at least one other active ingredient

BACKGROUND OF THE INVENTION 1,4-Benzothiepine 1,1-dioxide compounds and the use thereof for the treatment of hyperlipidemia and of arteriosclerosis and hypercholesterolemia have been described in U.S. Pat. No. 6,221,897].

Antidiabetics are described in the Rote Liste 2001, chapter 12. More specifically, the antidiabetics include insulin and insulin derivatives such as, for example, Lantus® (see www.lantus.com) or fast-acting insulins (see U.S. Pat. No. 6,221,633), GLP-1 derivatives such as, for example, those disclosed in WO 98/08871, and orally active hypoglycemic active ingredients. The orally active hypoglycemic active ingredients include, preferably, sulfonylureas, biguanides, meglitinides, oxadiazolidinediones, thiazolidinediones, glucosidase inhibitors, glucagon antagonists, GLP-1-agonists, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and RXR agonists and active ingredients which act on the ATP-dependent potassium channel of the beta cells.

SUMMARY OF THE INVENTION

The present invention is directed to a 1,4-benzothiepine 1,1-dioxide compound of formula I

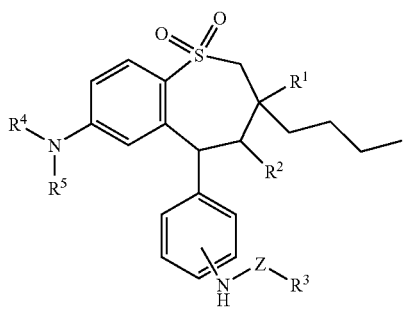

in which
R$^1$ is methyl, ethyl, propyl, or butyl;
R$^2$ is H, —OH, —NH$_2$, or —NH—(C$_1$–C$_6$)-alkyl;
R$^3$ is a saccharide residue, disaccharide residue, trisaccharide residue, or tetrasaccharide residue, wherein the saccharide residue, disaccharide residue, trisaccharide residue or tetrasaccharide residue is optionally substituted one or more times by a saccharide protective group; or amino acid residue, diamino acid residue, triamino acid residue, or tetraamino acid residue, wherein the amino acid residue, diamino acid residue, triamino acid residue or tetraamino acid residue is optionally substituted one or more times by an amino acid protective group;
R$^4$ is methyl, ethyl, propyl, or butyl;
R$^5$ is methyl, ethyl, propyl, or butyl;
Z is —(C═O)$_n$—CO—C$_0$–C$_{16}$-alkyl-, —(C═O)$_n$—C$_0$–C$_{16}$-alkyl-NH—, —(C═O)$_n$—C$_0$–C$_{16}$-alkyl-O—, —(C═O)$_n$C$_1$–C$_{16}$-alkyl-(C═O)$_m$—, or a covalent bond;
n is 0 or 1; and
m is 0 or 1; or a pharmaceutically acceptable salt or physiologically functional derivative thereof, with at least one other active ingredient, or a pharmaceutically acceptable salt or physiologically functional derivative thereof. The invention is also directed to the use of the combination product, pharmaceutical composition comprising the combination product and method for preparing the pharmaceutical composition.

DETAILED DESCRIPTION OF THE INVENTION

Definitions of Terms

As used above, and throughout the description of the invention, the following terms, unless otherwise indicated, shall be understood to have the following meanings.

"Pharmaceutically acceptable salt", because of its greater solubility in water compared with the initial compound, means a salt that is particularly suitable for medical applications. The salt must have a pharmaceutically acceptable anion or cation. A suitable pharmaceutically acceptable salt as an acid addition salt of a compound of the invention, for example, is a salt of an inorganic acid such as hydrochloric acid, hydrobromic, phosphoric, metaphosphoric, nitric, sulfamic or sulfuric acid, or of organic acids such as, for example, acetic, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric or trifluoroacetic acid. The chloride salt is particularly preferably used for medical purposes. A suitable pharmaceutically acceptable salt as a base addition salt of a compound of the invention, for example, is an ammonium, alkali metal (such as sodium and potassium) and alkaline earth metal (such as magnesium and calcium) salt.

A salt with a pharmaceutically unacceptable anion likewise belongs in the scope of the invention as useful intermediates for the preparation or purification of a pharmaceutically acceptable salt or for use in nontherapeutic, for example in vitro, applications.

"Patient" means a mammal including a human.

"Physiologically functional derivative" means any physiologically tolerated derivative of a compound of the invention, e.g.,a prodrug such as an ester that is able on administration to a patient, to form (directly or indirectly) such a compound or an active metabolite thereof.

A prodrug of the compounds according to the invention are another aspect of this invention. Such prodrugs can be metabolized in vivo to give a compound according to the invention. These prodrugs may or may not be active themselves.

The a compound of formula I can also exist in various polymorphous forms, for example as amorphous and crystalline polymorphous forms. All the polymorphous forms of the compounds according to the invention are included in the scope of the invention and are a further aspect of the invention.

All references to "compound(s) according to formula I" in the following text relate to compound(s) of the formula I as described above and their salts, solvates and physiologically functional derivatives as described herein.

"Saccharide residue" means a compound derived from an aldose and ketose which has 3 to 7 carbon atoms and may belong to the D or L series; these include an amino saccharide, sugar alcohol or saccharic acid. Examples of saccharide residues are glucose, mannose, fructose, galactose, ribose, erythrose, glyceraldehyde, sedoheptulose, glucosamine, galactosamine, glucuronic acid, galacturonic acid, gluconic acid, galactonic acid, mannonic acid, glucamine, 3-amino-1,2-propanediol, glucaric acid and galactaric acid. The saccharide residue may also be substituted or protected.

"Di-, tri, or tetrasaccharide" means a saccharide composed respectively of two, three or four saccharide units. Di-, tri-, or tetrasaccharides are produced by acetal-like linkage with 2 or more sugars. The linkages may moreover occur in the α or β form. Examples of the polysaccharides are lactose, maltose and cellobiose.

"Substituted or protected saccharide" means a saccharide substituted or protected preferably on the hydrogen atom of an OH group of the saccharide. A suitable protective group for a hydroxyl group of a saccharide include the following: benzyl, acetyl, benzoyl, pivaloyl, trityl, tert-butyldimethylsilyl, benzylidene, cyclohexylidene and isopropylidene protective group.

"Amino acid" means, e.g., the stereoisomeric forms, i.e., D or L forms, of the following compounds:

azagly-NH2 is a compound of the formula NH2—HN—CONH2 and D-Asp is the D form of aspartic acid. According to their chemical nature, peptides are amides and decompose into amino acids on hydrolysis.

"Di-, tri-, and tetraamino acid residue" mean peptides composed of 2 to 4 of the abovementioned amino acids.

A suitable "amino acid protective group" (see, for example, T. W. Greene, "Protective Groups in Organic Synthesis", $2^{nd}$ Edition, John Wiley and Sons, New York 1991) for an amino acid are represented in the parentheses after the following abbreviated amino acid:

Arg(Tos), Arg(Mts), Arg(Mtr), Arg(PMV), Asp(OBzl), Asp (OBut), Cys(4-MeBzl), Cys(Acm), Cys(SBut), Glu(OBzl), Glu(OBut), His(Tos), His(Fmoc), His(Dnp), His(Trt), Lys (CI-2), Lys(Boc), Met(O), Ser(Bzl), Ser(But), Thr(Bzl), Thr(But), Trp(Mts), Trp(CHO), Tyr(Br-Z), Tyr(Bzl) or Tyr (but). Furthermore, amino protective groups used are preferably the benzyloxycarbonyl(Z) radical that is removable by catalytic hydrogenation, the 2-(3,5-dimethyloxyphenyl) prop-2-yloxycarbonyl (Ddz) or trityl (Trt) radical that is removed by a weak acid and the 9-fluorenylmethyloxycarbonyl (Fmoc) radical that is removed by a secondary amine.

"Other active ingredient" that is suitable for the combination products means:

all antidiabetics such as those mentioned in the Rote Liste 2001, chapter 12. Most of the other active ingredients listed below are disclosed in the USP Dictionary of USAN and International Drug Names, US Pharmacopeia, Rockville 2001. More specifically, the antidiabetics include insulin and insulin derivatives such as, for example, Lantus® (see www.lantus.com) or fast-acting insulins (see U.S. Pat. No. 6,221,633), GLP-1 derivatives such as, for example, those disclosed in WO 98/08871, and orally active hypoglycemic

| alanine | glycine | | proline | | |
|---|---|---|---|---|---|
| cysteine | | histidine | | | glutamine |
| aspartic acid | | isoleucine | | | arginine |
| glutamic acid | | lysine | | | serine |
| phenylalanine | leucine | | threonine | | |
| tryptophan | | methionine | | | valine |
| tyrosine | asparagine | | | | |
| 2-aminoadipic acid | | | | 2-aminoisobutyric acid | |
| 3-aminoadipic acid | | | | 3-aminoisobutyric acid | |
| beta-alanine | | | | 2-aminopimelic acid | |
| 2-aminobutyric acid | | | | 2,4-diaminobutyric acid | |
| 4-aminobutyric acid | | | | desmosine | |
| piperidic acid | | | | 2,2-diaminopimelic acid | |
| 6-aminocaproic acid | | | | 2,3-diaminopropionic acid | |
| 2-aminoheptanoic acid | | | N-ethylglycine | | |
| 2-(2-thienyl)-glycine | | | | 3-(2-thienyl)-alanine | |
| penicillamine | | | | sarcosine | |
| N-ethylasparagine | | | | N-methylisoleucine | |
| hydroxylysine | | | 6-N-methyllysine | | |
| allo-hydroxylysine | | | | N-methylvaline | |
| 3-hydroxyproline | | | | norvaline | |
| 4-hydroxyproline | | | | norleucine | |
| isodesmosine | | | ornithine | | |
| allo-isoleucine | | | | | |
| N-methylglycine. | | | | | |

Abbreviated names for the amino acids follow the generally customary names (cf. Schröder, Lübke, The Peptides, Vol. 1, New York 1965, pages XXII–XXIII; Houben-Weyl, Methoden der Organischen Chemie [Methods of Organic Chemistry], Volume XV/1 and 2, Stuttgart 1974). The amino acid pGlu is pyroglutamyl, Nal is 3-(2-naphthyl)alanine, active ingredients. The orally active hypoglycemic active ingredients include, preferably, sulfonylureas, biguanides, meglitinides, oxadiazolidinediones, thiazolidinediones, glucosidase inhibitors, glucagon antagonists, GLP-1-agonists, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and RXR agonists and active ingredients which act on the ATP-dependent potassium channel of the beta cells.

EMBODIMENTS

A preferred embodiment of the invention is where the 1,4-benzothiepine 1,1-dioxide compound of formula I and other active ingredient of the combination product displays an activity that is synergistic. Further preferred is where the hypolipidemic activity of the 1,4-benzothiepine 1,1-dioxide compound of formula I in the combination product is increased synergistically to a disproportionately large extent by the other active ingredient.

Another preferred embodiment of the invention is where the other active ingredient is an orally active hypoglycemic.

Another preferred embodiment of the invention is where the combination product comprises the compound of formula I wherein:

$R^1$ ethyl, propyl, or butyl; and
$R^3$ is a saccharide residue, or disaccharide residue, wherein the saccharide residue or disaccharide residue is optionally substituted one or more times by a saccharide protective group; or amino acid residue, or diamino acid residue, wherein the amino acid residue or diamino acid residue is optionally substituted one or more times by an amino acid protective group; or a pharmaceutically acceptable acid addition salt thereof.

A further preferred embodiment of the invention is where the combination product comprises the compound of formula I in which:

$R^1$ ethyl;
$R^2$ OH;
$R^3$ is a saccharide residue, wherein the saccharide residue is optionally substituted one or more times by a saccharide protective group;
diamino acid residue, wherein the diamino acid residue is optionally substituted one or more times by an amino acid protective group;
$R^4$ methyl;
$R^5$ methyl; and
Z—(C=O)—$C_0$–$C_4$-alkyl, a covalent bond; or a pharmaceutically acceptable acid addition salts thereof.

Another particular embodiment of the invention is where the compound of formula I is administered in combination with an HMG-CoA reductase inhibitor such as simvastatin, fluvastatin, pravastatin, lovastatin, atorvastatin, cerivastatin, or rosuvastatin.

Another particular embodiment of the invention is where the compound of formula I is administered in combination with a cholesterol absorption inhibitor such as, for example, ezetimibe, tiqueside, or pamaqueside.

Another particular embodiment of the invention is where the compound of formula I is administered in combination with a PPAR gamma agonist such as, for example, rosiglitazone, pioglitazone, JTT-501 (see Table II), or GI 262570 (see Table II).

Another particular embodiment of the invention is where the compound of formula I is administered in combination with PPAR alpha agonists such as, for example, GW 9578 (see Table I), or GW 7647 (see Table I).

Another particular embodiment of the invention is where the compound of formula I is administered in combination with a mixed PPAR alpha/gamma agonist such as, for example, GW 1536 (see Table I), AVE 8042, AVE 8134, or AVE 0847, or as described in PCT/US 11833, PCT/US 11490, or DE10142734.4.

Another particular embodiment of the invention is where the compound of formula I is administered in combination with a fibrate such as, for example, fenofibrate, clofibrate, or bezafibrate.

Another particular embodiment of the invention is where the compound of formula I is administered in combination with an MTP inhibitor such as, for example, implitapide, BMS 201038 (see Table I), or R 103757 (see Table I).

Another particular embodiment of the invention is where the compound of formula I is administered in combination with bile acid absorption inhibitors (see, for example, U.S. Pat. No. 6,245,744 or U.S. Pat. No. 6,221,897) such as, for example, HMR 1741.

Another particular embodiment of the invention is where the compound of formula I is administered in combination with a CETP inhibitor such as, for example, JTT-705 (see Table II).

Another particular embodiment of the invention is where the compound of formula I is administered in combination with a polymeric bile acid adsorbent such as, for example, cholestyramine, or colesevelam.

Another particular embodiment of the invention is where the compound of formula I is administered in combination with an LDL receptor inducer (see U.S. Pat. No. 6,342,512) such as, for example, HMR1171, or HMR1586.

Another particular embodiment of the invention is where the compound of formula I is administered in combination with an ACAT inhibitor such as, for example, avasimibe.

Another particular embodiment of the invention is where the compound of formula I is administered in combination with an antioxidant such as, for example, OPC 14117 (see Table II).

Another particular embodiment of the invention is where the compound of formula I is administered in combination with a lipoprotein lipase inhibitor such as, for example, NO 1886 (see Table II).

Another particular embodiment of the invention is where the compound of formula I is administered in combination with an ATP-citrate lyase inhibitor such as, for example, SB 204990 (see Table II).

Another particular embodiment of the invention is where the compound of formula I is administered in combination with a squalene synthetase inhibitor such as, for example, BMS 188494 (see Table II).

Another particular embodiment of the invention is where the compound of formula I is administered in combination with a lipoprotein(a) antagonist such as, for example, CI 1027 (see Table II) or nicotinic acid.

Another particular embodiment of the invention is where the compound of formula I is administered in combination with a lipase inhibitor such as, for example, orlistat.

Another particular embodiment of the invention is where the compound of formula I is administered in combination with insulin.

Another particular embodiment of the invention is where the compound of formula I is administered in combination with a sulfonylurea such as, for example, tolbutamide, glibenclamide, glipizide or glimepiride.

Another particular embodiment of the invention is where the compound of formula I is administered in combination with a biguanide such as, for example, metformin.

Another particular embodiment of the invention is where the compound of formula I is administered in combination with a meglitinide such as, for example, repaglinide.

Another particular embodiment of the invention is where the compound of formula I is administered in combination with a thiazolidinedione such as, for example, troglitazone, ciglitazone, pioglitazone, rosiglitazone or the compounds disclosed in WO 97/41097, in particular 5-[[4-[(3,4-dihydro-3-methyl-4-oxo-2-quinazolinylmethoxy]phenyl]methyl]-2,4-thiazolidinedione.

Another particular embodiment of the invention is where the compound of formula I is administered in combination with an a-glucosidase inhibitor such as, for example, miglitol or acarbose.

Another particular embodiment of the invention is where the compound of formula I is administered in combination with an active ingredient which acts on the ATP-dependent potassium channel of the beta cells, such as, for example, tolbutamide, glibenclamide, glipizide, glimepiride or repaglinide.

Another particular embodiment of the invention is where the compound of formula I is administered in combination with more than one of the aforementioned compounds, e.g., in combination with a sulfonylurea and mefformin, a sulfonylurea and acarbose, repaglinide and mefformin, insulin and a sulfonylurea, insulin and mefformin, insulin and troglitazone, insulin and lovastatin, etc.

Another further particular embodiment of the invention is where the compound of formula I is administered in combination with CART modulators (see "Cocaine-amphetamine-regulated transcript influences energy metabolism, anxiety and gastric emptying in mice" Asakawa, A, et al., M.:Hormone and Metabolic Research (2001), 33(9), 554-558), NPY antagonists, e.g. naphthalene-1-sulfonic acid {4-[(4-aminoquinazolin-2-ylamino)methyl] cyclohexylmethyl}amide; hydrochloride (CGP 71683A)), MC4 agonists (e.g. 1-amino-1,2,3,4-tetrahydronaphthalene-2-carboxylic acids [2-(3a-benzyl-2-methyl-3-oxo-2,3,3a,4, 6,7-hexahydropyrazolo[4,3-c]pyridin-5-yl)-1-(4-chlorophenyl)-2-oxo-ethyl]amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3-agonists (e.g. 1-(4-chloro-3-methanesulfonylmethylphenyl)-2-[2-(2,3-dimethyl-1 H-indol-6-yloxy)ethylamino]hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)); serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1 H-isoquinoline-2carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

Another particular embodiment of the invention is where the other active ingredient is leptin, see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

Another particular embodiment of the invention is where the other active ingredient is dexamphetamine or amphetamine.

Another particular embodiment of the invention is where the other active ingredient is fenfluramine or dexfenfluramine.

Another particular embodiment of the invention is where the other active ingredient is sibutramine.

Another particular embodiment of the invention is where the other active ingredient is orlistat.

Another particular embodiment of the invention is where the other active ingredient is mazindol or phentermine.

Another particular embodiment of the invention is where the compound of formula I is administered in combination with dietary fiber materials, preferably insoluble dietary fiber materials (see, for example, Carob/Caromax® (Zunft H J; et al., Carob pulp preparation for treatment of hypercholesterolemia, ADVANCES IN THERAPY (2001 Sep-Oct), 18(5), 230–6.) Caromax is a carob-containing product supplied by Nutrinova, Nutrition Specialties & Food Ingredients GmbH, Industriepark Höchst, 65926 Frankfurt/Main)). Combination with Caromax® is possible in one preparation or by a separate administration of a compound of formula I and Caromax®. Caromax® can moreover be administered in the form of foodstuffs such as, for example, in bakery products or muesli bars. Combination of a compound of formula I with Caromax® not only improves the effect, in particular in LDL-cholesterol lowering, compared with the individual active ingredients, but is also tolerated better.

TABLE I
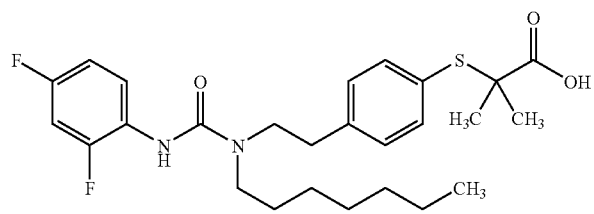
GW-9578
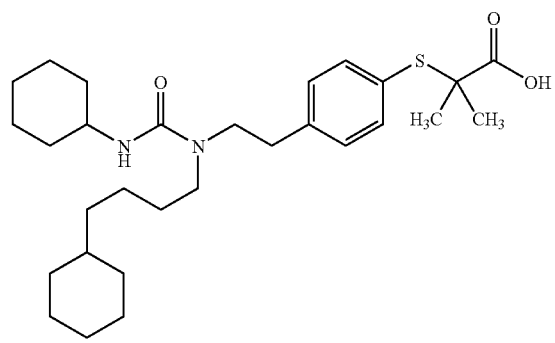
GW-7647
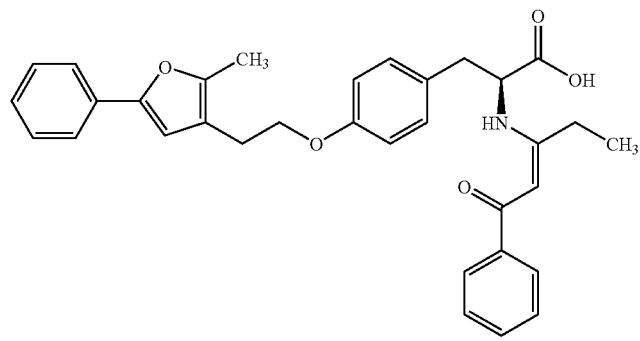
GW-1536
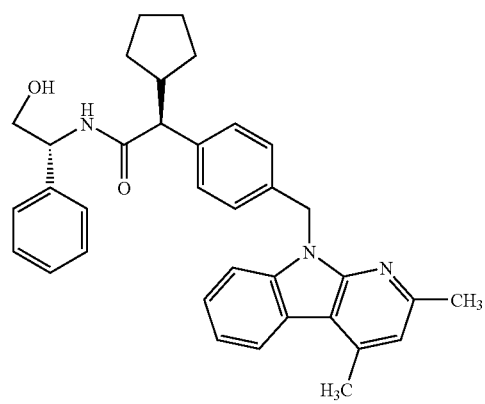
Implitapide TABLE I-continued
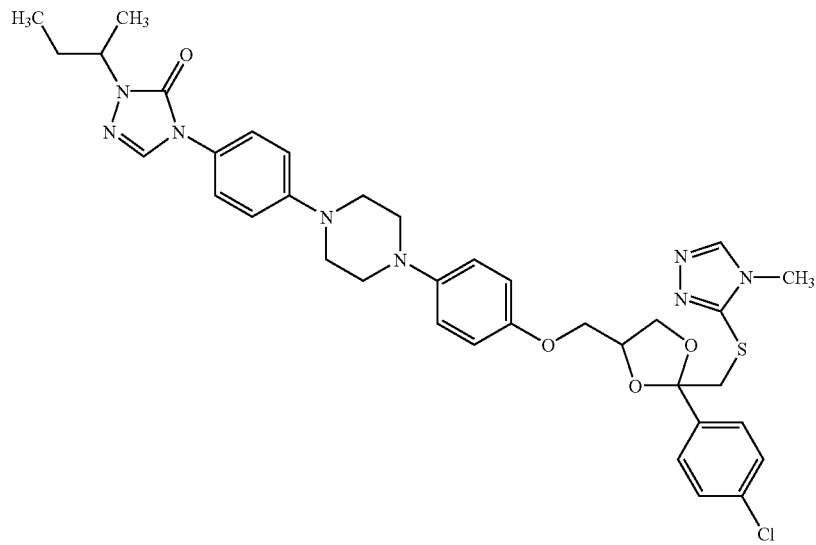
R-103757
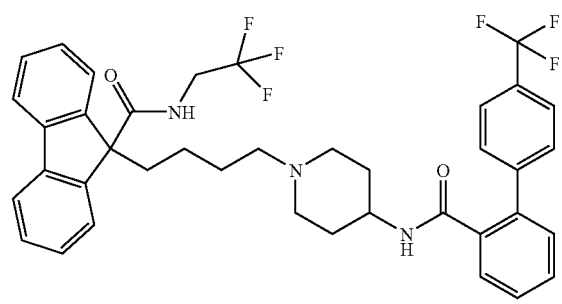
BMS-201038
TABLE II
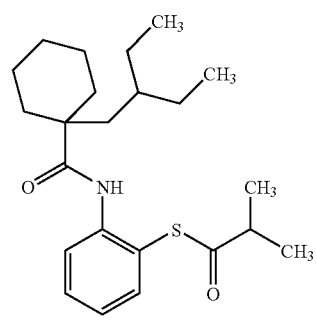
JTT-705

TABLE II-continued
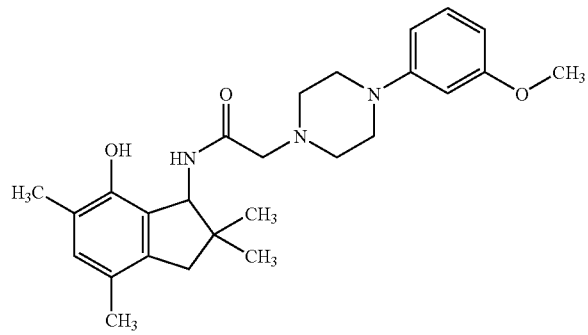
OPC-14117
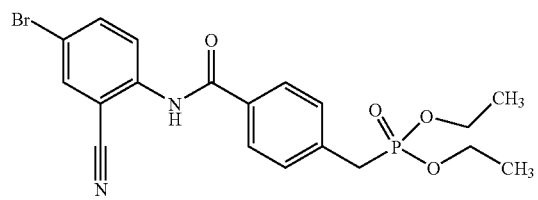
NO-1886
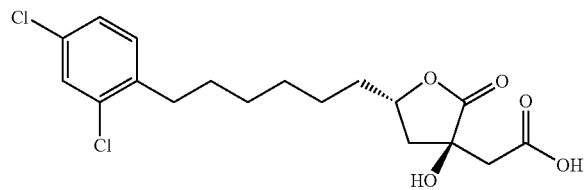
SB-204990
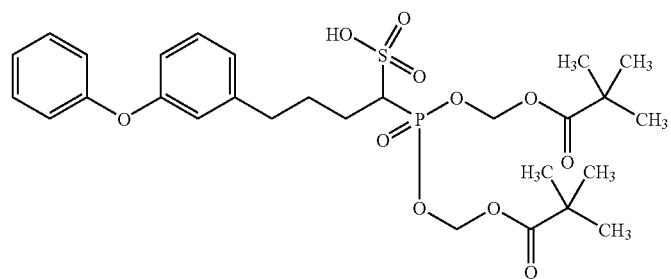
BMS-188494
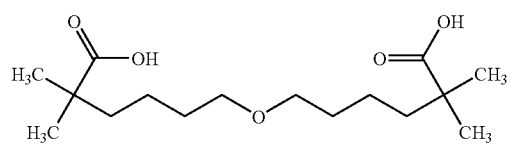
CI-1027

TABLE II-continued

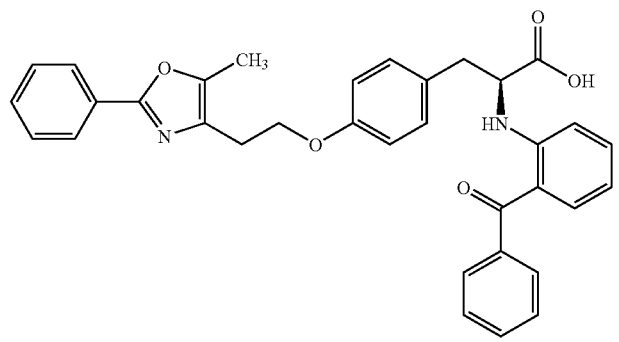

GI 262570

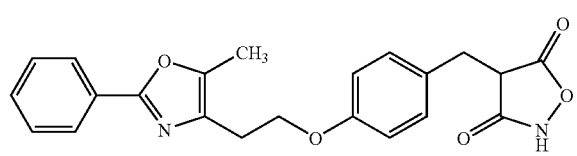

JTT-501

The amount of a compound of formula I and of the other active ingredient necessary to achieve the desired biological effect with the combination product depends on a number of factors, e.g., the specific compound of formula I or other active ingredient chosen, the intended use, the mode of administration and the clinical condition of the patient. The daily dose is generally in the range from 0.1 to 100 mg (typically from 0.1 to 50 mg) per day per kilogram of body weight, e.g. 0.1–10 mg/kg/day. Tablets or capsules may contain, for example, from 0.01 to 100 mg, typically from 0.02 to 50 mg. In the case of a pharmaceutically acceptable salt, the aforementioned weight data are based on the weight of the compound of formula I or other active ingredient derived from the salt. The compound of formula I or other active ingredient of the combination product, however, is preferably in the form of a pharmaceutical composition with a convertible carrier. The carrier must, of course, be compatible in the sense that it is compatible with the compound of formula I or other active ingredient of the combination product and is not harmful for the patient's health. The carrier may be a solid or a liquid or both and is preferably formulated with the compound as single dose, for example as a tablet, which contain from 0.05% to 95% by weight of the other active ingredient. Other pharmaceutically active substances may likewise be present, including other compound of formula I. The pharmaceutical combination product of the invention can be produced by one of the known pharmaceutical methods which consist essentially of mixing the compound of formula I or other active ingredient with pharmacologically acceptable carriers and/or excipients.

Pharmaceutical combination product of the invention is one suitable for oral and peroral (e.g. sublingual) administration, although the most suitable mode of administration depends in each individual case on the nature and severity of the condition to be treated and on the nature of the particular compound of formula I used. Coated formulations and coated slow-release formulations of the combination product are also within the scope of the invention. Acid- and gastric juice-resistant formulations are preferred. Suitable gastric juice-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compositions comprising the compound of formula I or other active ingredient for oral administration may be in the form of separate units such as, for example, capsules, cachets, lozenges or tablets, each of which contain a defined amount of the compound of the formula (I) and of the other active ingredient; as powders or granules; as a solution or suspension in an aqueous or nonaqueous liquid; or as an oil-in-water or water-in-oil emulsion. The combination product may, as already mentioned, be prepared by any suitable pharmaceutical method which includes a step in which the compound of formula I or other active ingredient and the carrier (which may consist of one or more additional ingredients) are brought into contact. The combination product is generally produced by a uniform and homogeneous mixing of the compound of formula I or other active ingredient with a liquid and/or finely divided solid carrier, after which the product is shaped if necessary. Thus, for example, a tablet can be produced by compressing or shaping a powder or granules of the compound, and the other ingredient. Compressed tablets may be produced by tableting the compound of formula I or other active ingredient in free-flowing form, such as, for example, a powder or granules, where appropriate mixed with a binder, glidant, inert diluent and/or one (or more) surface-active/dispersing agent in a suitable machine. Shaped tablets can be produced by shaping the compound of formula I or other active ingredient which is in powder form and has been moistened with an inert liquid diluent in a suitable machine.

Pharmaceutical composition of combination products suitable for peroral (sublingual) administration include lozenges which contain a cderivature of formula I and the other active ingredient with a flavoring, normally sucrose and gum arabic or tragacanth, and pastilles which comprise the compound of formula I or other active ingredient in an inert base such as gelatin and glycerol or sucrose and gum arabic.

Other active ingredients may be combined with a compound of formula I in particular for synergistic improvement of the effect. Administration of the other active ingredient combination and the compound of formula I can also take place either by separate administration of the other active ingredient and the compound of formula I to the patient, i.e., an in vivo formation of a combination product, or in the form of a combination product in which the other active ingredient and compound of formula I are present in one pharmaceutical preparation. When the administration of the other active ingredient combination and the compound of formula I takes place by separate administration such administration should be undertaken so that the effects of each combine additively or synergistically, preferably synergistically. Thus, the separate administration is preferably undertaken closely in time, e.g., within 10 minutes of each other.

The combined use of the compound of formula I and the other active ingredient are used for the therapeutic purposes noted herein in a patient, such that the combination is present in a pharmaceutically effective amount. That pharmaceutically effective amount arises from the use of the compound of formula I and the other active ingredient wherein each is used in a pharmaceutically effective amount, or by virtue of additive or synergistic effects arising from the combined use, each can also be used in a subclinical pharmaceutically effective amount, i.e., an amount that, if used alone, provides for reduced or ineffective pharmaceutical effectiveness for the therapeutic purposes noted herein, provided that the combined use is pharmaceutically effective. In addition, the present invention encompasses the use of the combination of the compound of formula I and the other active ingredient as described herein, where the compound of formula I or the other active ingredient is present in a pharmaceutically effective amount, and the other is present in a subclinical pharmaceutically effective, provided that the combined use is pharmaceutically effective owing to their additive or synergistic effects. As used herein, the term "additive effect" describes the combined effect of two (or more) pharmaceutically active agents that is equal to the sum of the effect of each agent given alone. A syngergistic effect is one in which the combined effect of two (or more) pharmaceutically active agents is greater than the sum of the effect of each agent given alone. It is self-evident that every suitable combination of a compound of formula I with one or more of the aforementioned other active ingredients and optionally with one or more other pharmacologically active substances is to be regarded as covered by the scope of protection of the present invention.

The combination products comprising a compound of formula I represent ideal medicaments for the treatment of lipid metabolism disorders and/or carbohydrate metabolism disorders, especially hyperlipidemia or metabolic syndrome. The combination products are likewise suitable for modulating the decrease of the serum cholesterol level or for the prevention or treatment of arteriosclerotic manifestations.

The following preparations serve to illustrate the invention without, however, restricting it.

EXAMPLE A

Soft gelatin capsules containing 100 mg of the compound of formula I and other active ingredient per capsule:

|  | per capsule |
|---|---|
| the compound of formula I and other active ingredient | 100 mg |
| triglyceride mixture fractionated from coconut fat | 400 mg |
| capsule contents | 500 mg |

EXAMPLE B

Emulsion containing 60 mg of the compound of formula I and other active ingredient per 5 ml:

|  | per 100 ml of emulsion |
|---|---|
| the compound of formula I and other active ingredient | 1.2 g |
| neutral oil | q.s. |
| sodiumcarboxymethylcellulose | 0.6 g |
| polyoxyethylene stearate | q.s. |
| glycerol, pure | 0.2 to 2.0 g |
| flavoring | q.s. |
| water (deionized or distilled) | ad 100 ml |

EXAMPLE C

Rectal drug form containing 40 mg of the compound of formula I and other active ingredient per suppository:

|  | per suppository |
|---|---|
| the compound of formula I and other active ingredient | 40 mg |
| suppository base | ad 2 g |

EXAMPLE D

Tablets containing 40 mg of the compound of formula I and other active ingredient per tablet:

|  | per tablet |
|---|---|
| the compound of formula I and other active ingredient | 40 mg |
| lactose | 600 mg |
| corn starch | 300 mg |
| soluble starch | 20 mg |
| magnesium stearate | 40 mg |
|  | 1000 mg |

EXAMPLE E

Coated tablets containing 50 mg of the compound of formula I and other active ingredient per coated tablet:

|  | per coated tablet |
|---|---|
| the compound of formula I and other active ingredient | 50 mg |
| corn starch | 100 mg |
| lactose | 60 mg |
| sec. calcium phosphate | 30 mg |
| soluble starch | 5 mg |
| magnesium stearate | 10 mg |
| colloidal silica | 5 mg |
|  | 260 mg |

EXAMPLE F

The following formulations are suitable for producing the contents of hard gelatin capsules:

| | |
|---|---|
| a) the compound of formula I and other active ingredient | 100 mg |
| corn starch | 300 mg |
| | 400 mg |
| b) the compound of formula I and other active ingredient | 140 mg |
| lactose | 180 mg |
| corn starch | 180 mg |
| | 500 mg |

EXAMPLE G

Drops can be produced using the following formulation (100 mg of the compound of formula I and other active ingredient in 1 ml =20 drops):

| | |
|---|---|
| the compound of formula I and other active ingredient | 10 g |
| methyl benzoate | 0.07 g |
| ethyl benzoate | 0.03 g |
| ethanol, 96% | 5 ml |
| demineralized water | ad 100 ml |

Experimental

The synergistic activity of the combination product of a compound of formula I with the other active ingredient was tested in an animal experiment. For this purpose, compound V1 from the compound of formula I was tested:

Hamsters were used for the biological testing of the combination product of the invention. Male Syrian hamsters (*Mesocricetus auratus*) from 8 to 10 weeks of age were used for the experiment. The animals received a standard feed (Teklad 8604M) supplemented with 0.1% cholesterol. An additional normal control group received only standard feed.

The test substances were administered orally by gavage once a day on 10 consecutive days, and the control group was treated with the vehicle.

Feces were collected on days 5 and 6 of the experiment for bile acid analysis. Retroorbital blood was taken from the animals on day 10 of the experiment, and the lipid levels in the plasma were determined. Radioactive tracers were administered orally to the animals on day 9 of the experiment to determine the cholesterol absorption in analocy to the method described by Zilversmith et al. On day 11 of the experiment, the animals were sacrificed, and the animals' livers were removed for cholesterol analysis and preparation of microsomes. The 7α-hydroxylase activity was determined in the liver microsomes ex vivo by a modified method of Hylemon et al.

Effect of ezetimibe (K00 04513) plus C1 on cholesterol absorption

Ezetimibe (K00 04513) is a cholesterol absorption inhibitor from Schering Plough

| 1 | Teklad | | Normal ctr. | n = 5 |
|---|---|---|---|---|
| 2 | Teklad | +0.1% CH | Cholesterol ctr. | n = 5 |
| 3 | Teklad | +0.1% CH | 0.1 mg/kg/d Ezetimibe (K004513) | n = 5 |
| 4 | Teklad | +0.1% CH | 0.1 mg/kg/d V1 | n = 5 |
| 5 | Teklad | +0.1% CH | 0.3 mg/kg/d V1 | n = 5 |
| 6 | Teklad | +0.1% CH | 1 mg/kg/d V1 | n = 5 |
| 7 | Teklad | +0.1% CH | 0.1 mg/kg/V1 + 0.1 mg/kg/d K0004513 | n = 5 |
| 8 | Teklad | +0.1% CH | 0.1 mg/kg/V1 + 0.3 mg/kg/d K0004513 | n = 5 |
| 9 | Teklad | +0.1% CH | 0.1 mg/kg/V1 + 1 mg/kg/d K0004513 | n = 5 |

K00004513 employed as stock solution (1 mg/ml in EtOH) Substances are dissolved in 2% EtOH in a final concentration of 5%.

The solutions are then suspended with 0.4% potato starch. Administration takes place 1× in the morning with 10 ml/kg Feed: Teklad 8604M CH: 032201 M Experimental animals: Male Syrian hamsters (*Mesocricetus auratus*) supplied by Harlan 100–120 g at the start of adaptation

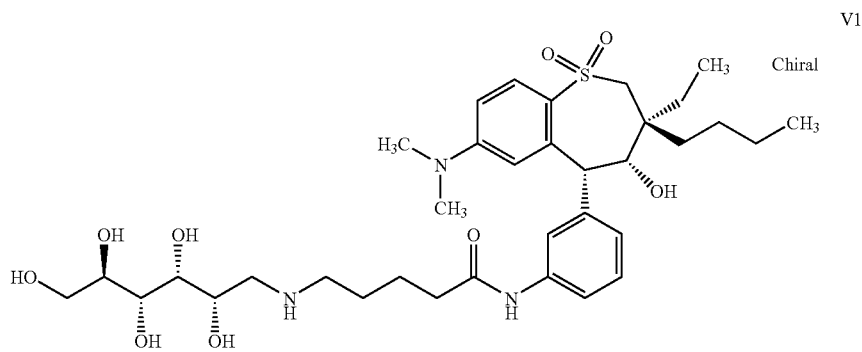

Measured Parameters:

Feed consumption

Animal weight (weekly)

Liver weight

Safety parameters (CH; TG; ALAT/ASAT; AP; HDULDL)

Liver cholesterol (HPLC)=1×500 mg in EtOH/KOH

CYP7 activity (liver microsomes as group pool of 0.5 g each—preparation on day of experiment)

Feces collected on day 5–7 for bile acid determination

| Group | Feed/Product | Plasma-parameter | | | | | | |
|---|---|---|---|---|---|---|---|---|
| | | Cholesterol mmol/L | STD | % | Triglycerides mmol/L | STD | % | LDL mmol/L |
| 1 | Normal ctr. | 2.84 | ±0.09 | 81 | 2.01 | ±0.23 | 124 | 0.60 |
| 2 | Cholesterol ctr. + 0.1% CH | 3.50 | ±0.27 | 100 | 1.62 | ±0.54 | 100 | 1.12 |
| 3 | + 0.1% CH 0.1 mg/kg/d Ezetimibe (K0004513) | 3.44 | ±0.64 | 98 | 1.63 | ±0.36 | 100 | 1.04 |
| 4 | + 0.1% CH 0.1 mg/kg/d V1 | 4.20 | ±1.46 | 120 | 1.87 | ±0.30 | 115 | 1.06 |
| 5 | + 0.1% CH 0.3 mg/kg/d V1 | 4.01 | ±0.89 | 114 | 1.75 | ±0.23 | 108 | 1.18 |
| 6 | + 0.1% CH 1 mg/kg/d V1 | 3.23 | ±0.19 | 92 | 2.02 | ±0.57 | 124 | 0.92 |
| 7 | + 0.1% CH 0.1 mg/kg/d V1 + 0.1 mg/kg/d Ezetimibe | 3.62 | ±0.18 | 103 | 2.08 | ±0.12 | 128 | 1.04 |
| 8 | + 0.1% CH 0.3 mg/kg/d V1 + 0.1 mg/kg/d Ezetimibe | 3.56 | ±0.94 | 101 | 2.11 | ±0.58 | 130 | 0.99 |
| 9 | + 0.1% CH 1 mg/kg/d V1 + 0.1 mg/kg/d Ezetimibe | 2.82 | ±0.05 | 81 | 1.84 | ±0.23 | 113 | 0.76 |

It is evident from the table that the compounds of the formula I in combination with ezetimibe show a synergistic effect on the plasma parameters.

The present invention may be embodied in other specific forms without departing from the spirit or essential attributes thereof.

What is claimed is:

1. A method for effecting the or treatment of a lipid metabolism disorder or metabolic syndrome in a patient comprising administering a pharmaceutically effective amount of a composition of matter comprising a compound of formula I

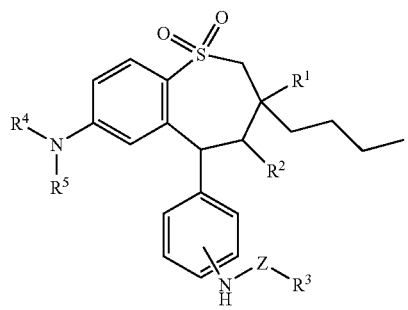

I in which
R$^1$ is methyl, ethyl, propyl, or butyl;
R$^2$ is H, —OH, —NH$_2$, or —NH—(C$_1$–C$_6$)-alkyl;
R$^3$ is a saccharide residue, disaccharide residue, trisaccharide residue, or tetrasaccharide residue, wherein the saccharide residue, disaccharide residue, trisaccharide residue or tetrasaccharide residue is optionally substituted one or more times by a saccharide protective group; or
amino acid residue, diamino acid residue, triamino acid residue, or tetraamino acid residue, wherein the amino acid residue, diamino acid residue, triamino acid residue or tetraamino acid residue is optionally substituted one or more times by an amino acid protective group;
R$^4$ is methyl, ethyl, propyl, or butyl;
R$^5$ is methyl, ethyl, propyl, or butyl;
Z is —(C=O)$_n$—C$_0$–C$_{16}$-alkyl-, —(C=O)$_n$—C$_0$–C$_{16}$-alkyl-NH—, —(C=O)$_n$—C$_0$–C$_{16}$-alkyl-O—, —(C=O)$_n$—C$_1$–C$_{16}$-alkyl-(C=O)$_m$—, or a covalent bond;
n is 0 or 1; and
m is 0 or 1; or
a pharmaceutically acceptable salt thereof, with at least one other active ingredient, or a pharmaceutically acceptable salt thereof, wherein the other active ingredient is selected from the group consisting of ezetimibe and carob pulp to the patient.

2. The method of claim 1 wherein the pharmaceutically effective amount of the composition of matter is provided for by the combination of a pharmaceutically effective amount or a subclinical pharmaceutically effective amount of the compound of formula I and a pharmaceutically effective amount or a subclinical pharmaceutically effective amount of the other active ingredient of the composition of matter, such that the combination results in the amount of the composition of matter being pharmaceutically effective.

3. A method for effecting the or treatment of hyperlipidemia in a patient comprising administering a pharmaceutically effective amount of a composition of matter comprising a compound of formula I

I in which
R$^1$ is methyl, ethyl, propyl, or butyl;
R$^2$ is H, —OH, —NH$_2$, or —NH—(C$_1$–C$_6$)-alkyl;

R³ is a saccharide residue, disaccharide residue, trisaccharide residue, or tetrasaccharide residue, wherein the saccharide residue, disaccharide residue, trisaccharide residue or tetrasaccharide residue is optionally substituted one or more times by a saccharide protective group; or
amino acid residue, diamino acid residue, triamino acid residue, or tetraamino acid residue, wherein the amino acid residue, diamino acid residue, triamino acid residue or tetraamino acid residue is optionally substituted one or more times by an amino acid protective group;

R⁴ is methyl, ethyl, propyl, or butyl;
R⁵ is methyl, ethyl, propyl, or butyl;
Z is —(C=O)$_n$—C$_0$–C$_{16}$-alkyl-, —(C=O)$_n$—C$_0$–C$_{16}$-alkyl-NH—, —(C=O)$_n$—C$_0$–C$_{16}$-alkyl-O—, —(C=O)$_n$—C$_1$–C$_{16}$-alkyl-(C=O)$_m$—, or a covalent bond;
n is 0 or 1; and
m is 0 or 1; or
a pharmaceutically acceptable salt thereof, with at least one other active ingredient, or a pharmaceutically acceptable salt thereof, wherein the other active ingredient is selected from ezetimibe and carob pulp to the patient.

4. The method of claim 3 wherein the pharmaceutically effective amount of the composition of matter is provided for by the combination of a pharmaceutically effective amount or a subclinical pharmaceutically effective amount of the compound of formula I and a pharmaceutically effective amount or a subclinical pharmaceutically effective amount of the other active ingredient of the composition of matter, such that the combination results in the amount of the composition of matter being pharmaceutically effective.

5. A method for effecting the or treatment of arteriosclerotic manifestations in a patient comprising administering a pharmaceutically effective amount of a composition of matter comprising a compound of formula I

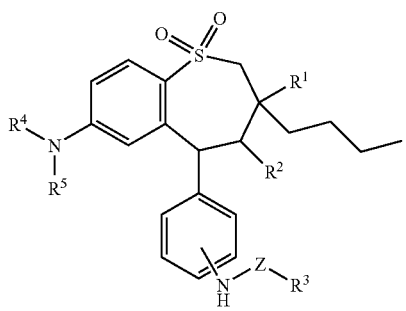

in which
R¹ is methyl, ethyl, propyl, or butyl;
R² is H, —OH, —NH₂, or —NH—(C₁–C₆)-alkyl;
R³ is a saccharide residue, disaccharide residue, trisaccharide residue, or tetrasaccharide residue, wherein the saccharide residue, disaccharide residue, trisaccharide residue or tetrasaccharide residue is optionally substituted one or more times by a saccharide protective group; or
amino acid residue, diamino acid residue, triamino acid residue, or tetraamino acid residue, wherein the amino acid residue, diamino acid residue, triamino acid residue or tetraamino acid residue is optionally substituted one or more times by an amino acid protective group;
R⁴ is methyl, ethyl, propyl, or butyl;
R⁵ is methyl, ethyl, propyl, or butyl;
Z is —(C=O)$_n$—C$_0$–C$_{16}$-alkyl-, —(C=O)$_n$—C$_0$–C$_{16}$-alkyl-NH—, —(C=O)$_n$—C$_0$–C$_{16}$-alkyl-O—, —(C=O)$_n$—C$_1$–C$_{16}$-alkyl-(C=O)$_m$—, or a covalent bond;
n is 0 or 1; and
m is 0 or 1; or
a pharmaceutically acceptable salt thereof, with at least one other active ingredient, or a pharmaceutically acceptable salt thereof, wherein the other active ingredient is selected from the group consisting of ezetimibe and carob pulp to the patient.

6. The method of claim 5 wherein the pharmaceutically effective amount of the composition of matter is provided for by the combination of a pharmaceutically effective amount or a subclinical pharmaceutically effective amount of the compound of formula I and a pharmaceutically effective amount or a subclinical pharmaceutically effective amount of the other active ingredient of the composition of matter, such that the combination results in the amount of the composition of matter being pharmaceutically effective.

7. A method for effecting the or treatment of a lipid metabolism disorder in a patient comprising administering a pharmaceutically effective amount of a composition of matter comprising a compound of formula I

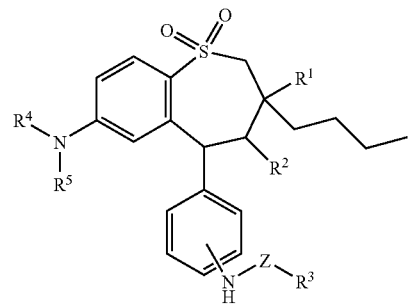

in which
R¹ is methyl, ethyl, propyl, or butyl;
R² is H, —OH, —NH₂, or —NH—(C₁–C₆)-alkyl;
R³ is a saccharide residue, disaccharide residue, trisaccharide residue, or tetrasaccharide residue, wherein the saccharide residue, disaccharide residue, trisaccharide residue or tetrasaccharide residue is optionally substituted one or more times by a saccharide protective group; or
amino acid residue, diamino acid residue, triamino acid residue, or tetraamino acid residue, wherein the amino acid residue, diamino acid residue, triamino acid residue or tetraamino acid residue is optionally substituted one or more times by an amino acid protective group;
R⁴ is methyl, ethyl, propyl, or butyl;
R⁵ is methyl, ethyl, propyl, or butyl;
Z is —(C=O)$_n$—C$_0$–C$_{16}$-alkyl-, —(C=O)$_n$—C$_0$–C$_{16}$-alkyl-NH—, —(C=O)$_n$—C$_0$–C$_{16}$-alkyl-O—, —(C=O)$_n$—C$_1$–C$_{16}$-alkyl-(C=O)$_m$—, or a covalent bond;
n is 0 or 1; and
m is 0 or 1; or
a pharmaceutically acceptable salt thereof, with at least one other active ingredient, or a pharmaceutically acceptable salt thereof, wherein the other active ingredient is selected from the group consisting of ezetimibe and carob pulp to the patient whereby the administering is effected by administering the compound of formula I and the other active ingredient of the composition of matter closely in time.

* * * * *